US012797240B2

(12) United States Patent
Jia et al.

(10) Patent No.: US 12,797,240 B2
(45) Date of Patent: Nov. 17, 2026

(54) SYSTEMS AND METHODS FOR DYNAMIC THERMAL COMPENSATION

(71) Applicant: Alcon Inc., Fribourg (CH)

(72) Inventors: Guangyao Jia, Irvine, CA (US); Ho Man Michael Fong, Irvine, CA (US); Kurt D. Leukanech, Laguna Niguel, CA (US); Colin Shane Wasson, Silverado, CA (US); Satish Yalamanchili, Irvine, CA (US)

(73) Assignee: Alcon Inc., Fribourg (CH)

( * ) Notice: Subject to any disclaimer, the term of this patent is extended or adjusted under 35 U.S.C. 154(b) by 308 days.

(21) Appl. No.: 18/782,278

(22) Filed: Jul. 24, 2024

(65) Prior Publication Data

US 2025/0041116 A1 Feb. 6, 2025

Related U.S. Application Data

(60) Provisional application No. 63/517,392, filed on Aug. 3, 2023.

(51) Int. Cl.

| | |
|---|---|
| ***A61F 9/007*** | (2006.01) |
| ***A61B 17/00*** | (2006.01) |
| ***A61B 90/00*** | (2016.01) |
| ***G16H 20/40*** | (2018.01) |
| ***G16H 40/63*** | (2018.01) |

(52) U.S. Cl.

CPC ......... *A61F 9/00745* (2013.01); *G16H 20/40* (2018.01); *G16H 40/63* (2018.01); *A61B 2017/0003* (2013.01); *A61B 2017/00088* (2013.01); *A61B 2017/00199* (2013.01); *A61B 2090/064* (2016.02); *A61B 2217/005* (2013.01); *A61B 2217/007* (2013.01)

(58) Field of Classification Search

CPC ........... A61F 9/00745; A61B 2090/064; A61B 2017/0003; A61B 2017/00088; A61B 2017/00199; A61B 2217/005; A61B 2217/007; G16H 20/40; G16H 40/63

See application file for complete search history.

(56) References Cited

U.S. PATENT DOCUMENTS

| | | | |
|---|---|---|---|
| 5,764,539 | A | 6/1998 | Rani |
| 6,941,813 | B2 | 9/2005 | Boukhny |
| 7,648,465 | B2 | 1/2010 | Gordon |
| 9,119,699 | B2 | 9/2015 | Gordon |
| 10,137,034 | B2 | 11/2018 | Heeren |
| 12,070,417 | B2 | 8/2024 | Gao |
| 2005/0285025 | A1 | 12/2005 | Boukhny et al. |
| 2017/0189231 | A1 | 7/2017 | Baxter |

(Continued)

*Primary Examiner* — Dung T Ulsh

(57) ABSTRACT

Embodiments of the present disclosure generally relate to systems and methods for measuring intraocular pressure (IOP) during ophthalmic surgery. In some embodiments, a method for measuring IOP is provided. The method includes measuring fluid pressure in a fluid flow path of a handpiece device using a pressure sensor disposed therein to obtain a fluid pressure measurement, determining a sensor temperature measurement of the pressure sensor, determining a predicted sensor zero offset based on the sensor temperature measurement using a determined zero offset correlation function, and adjusting the fluid pressure measurement with the predicted sensor zero offset to obtain an adjusted fluid pressure measurement.

15 Claims, 9 Drawing Sheets

(56) References Cited

U.S. PATENT DOCUMENTS

| | | | | |
|---|---|---|---|---|
| 2019/0104936 | A1 | 4/2019 | Gunn | |
| 2021/0204811 | A1 | 7/2021 | Cerboni | |
| 2022/0080099 | A1 * | 3/2022 | Govari | A61B 5/062 |
| 2022/0133537 | A1 | 5/2022 | Govari | |

* cited by examiner

SYSTEMS AND METHODS FOR DYNAMIC THERMAL COMPENSATION

BACKGROUND

During ophthalmic surgical procedures, fluids are often aspirated from the eye. For example, during vitreoretinal surgery, a vitrectomy probe may be used to aspirate vitreous material from the eye. As another example, during cataract surgery, a phacoemulsification probe may be used to fragment or emulsify a lens and to aspirate the broken or emulsified lens from the eye. In these or other procedures, to maintain intraocular pressure (IOP), a balanced salt solution (BSS) or other infusion/irrigation fluid may be introduced into the eye and removed during the procedure as part of the aspirated fluid.

Throughout such ophthalmic surgical procedures, a proper balance between the irrigation and aspiration of fluids to and from the eye should be effected to maintain an acceptable IOP in the eye. Aspirating fluid at a higher flow rate than the rate at which irrigating fluid is provided can result in a low IOP, and even a shallowing or collapse of the anterior chamber of the eye. In contrast, irrigating fluid into the eye at a higher flow rate than the rate at which fluid is being aspirated from the eye can result in high IOP and damage to the eye, such as rupture.

SUMMARY

Embodiments of the present disclosure generally relate to systems and methods relating to ophthalmic surgery and, more particularly, for measuring and monitoring fluid pressure in the eye during ophthalmic surgery.

In some embodiments, a method for measuring fluid pressure using a surgical system is provided. The method begins with measuring a fluid pressure in a fluid flow path of a handpiece device to obtain a fluid pressure measurement. The fluid pressure measurement is measured using a pressure sensor disposed on the fluid flow path in the handpiece device. The method then continues with determining a sensor temperature measurement of the pressure sensor, the sensor temperature measurement corresponding to a temperature of the pressure sensor when the fluid pressure was measured by the pressure sensor and determining a predicted sensor zero offset for the pressure sensor using a zero offset correlation function and the sensor temperature measurement. The zero offset correlation function comprises a mathematical polynomial function for providing the predicted sensor zero offset of the pressure sensor based on the sensor temperature measurement of the pressure sensor. Next, the method proceeds with adjusting the fluid pressure measurement with the predicted sensor zero offset, resulting in an adjusted fluid pressure measurement, and outputting the adjusted fluid pressure measurement.

In certain embodiments, a pressure sensor system for use with a handpiece device is provided. The pressure sensor system includes a pressure sensor disposed adjacent to a fluid flow path in the handpiece device. The pressure sensor system may be used for measuring a fluid pressure in the handpiece device and may include a flexible diaphragm having a pressure medium side and a circuit side, a sensing circuit having four semiconductor strain gages connected as a Wheatstone bridge, the sensing circuit in contact with the circuit side of the flexible diaphragm, a shunt resistor controlled by a shunt resistor switch and both electrically connected to the Wheatstone bridge, and an output shunt resistor controlled by an output shunt resistor switch and both electrically connected to the Wheatstone bridge.

The system also includes a memory and a processing unit connected to the pressure sensor. The memory may be programmed with a predetermined zero offset correlation function which may be used to provide a predicted sensor zero offset of the pressure sensor based on a temperature measurement of the pressure sensor. The processing unit may be configured to adjust a fluid pressure measurement from the pressure sensor by: receiving the fluid pressure measurement from the pressure sensor, determining a sensor temperature measurement of the pressure sensor, the sensor temperature measurement corresponding to a temperature of the pressure sensor when the fluid pressure measurement is obtained; determining the predicted sensor zero offset for the pressure sensor based on the sensor temperature measurement and using the predetermined zero offset correlation function stored in the memory; adjusting the fluid pressure measurement with the predicted sensor zero offset to obtain an adjusted fluid pressure measurement; and outputting the adjusted fluid pressure measurement.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
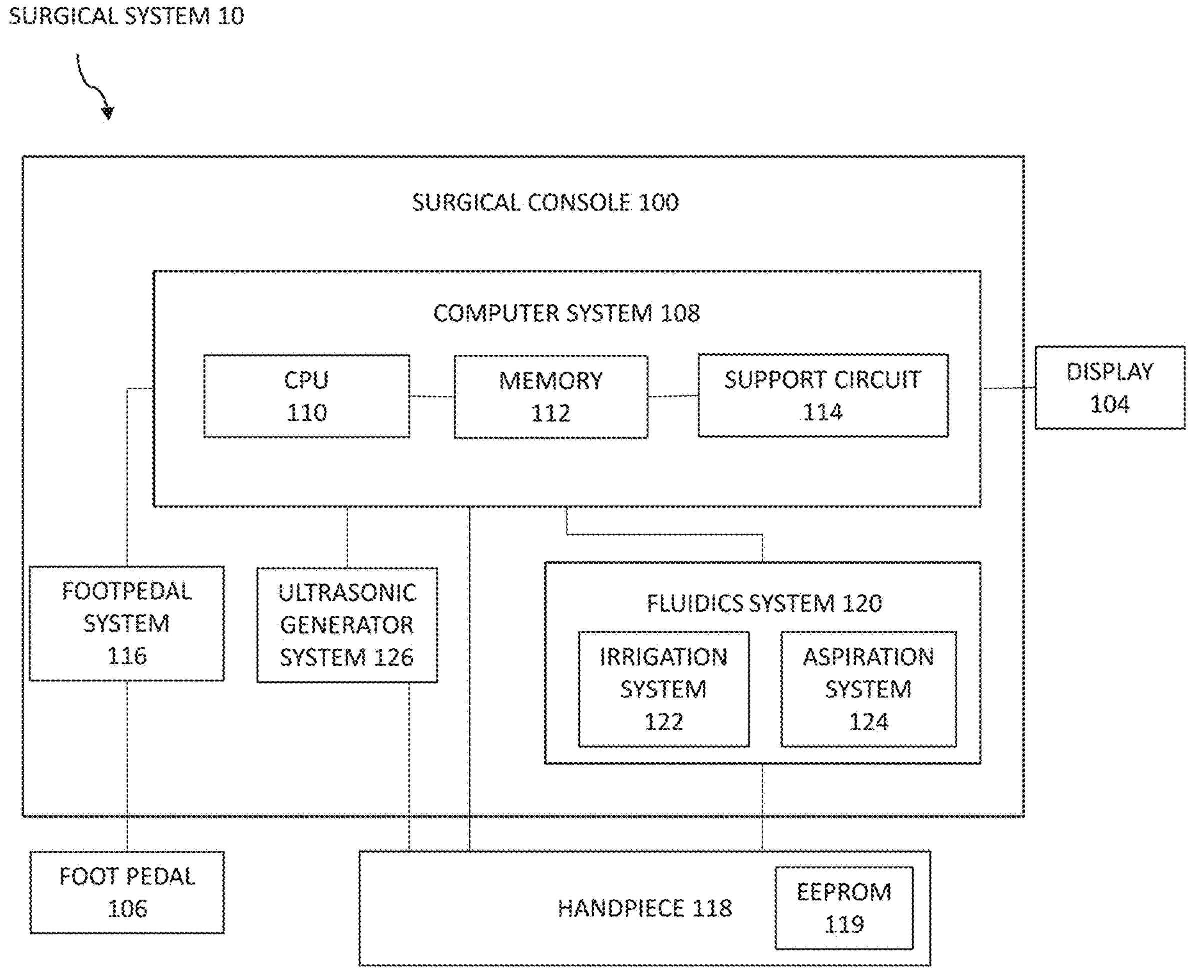
FIG. 1 is a schematic diagram of an exemplary system for use during an ophthalmic surgical procedure, according to certain embodiments of the present disclosure.

For the purposes of promoting an understanding of the principles of the disclosure, reference will now be made to the implementations illustrated in the drawings, and specific language will be used to describe the same. It will nevertheless be understood that no limitation of the scope of the disclosure is intended. Any alterations and further modifications to the described systems, devices, instruments, methods, and any further application of the principles of the present disclosure are fully contemplated as would normally occur to one skilled in the art to which the disclosure relates In particular, the features, components, and/or steps described with respect to one implementation may be combined with the features, components, and/or steps described with respect to other implantations of the disclosure. For simplicity, in some instances the same reference numbers are used throughout the drawings to refer to the same or like parts.

During ophthalmic surgeries, the irrigation and aspiration of fluids into and out of an eye contributes to the overall pressure within the eye or IOP. Accordingly, pressure within the irrigation and/or aspiration lines corresponds with, and may even be equivalent to, the IOP of the eye, and the IOP may therefore be indirectly monitored by measuring the fluid pressure within the irrigation and/or aspiration lines. One or more pressure sensors may therefore be operably connected to an irrigation and/or aspiration line for measuring and monitoring the IOP of a patient. In some examples, the pressure sensors may be integrated into surgical handpiece through which the irrigation and/or aspiration lines are disposed.

The positioning of a pressure sensor in a surgical handpiece enables the pressure sensor to be closer to the eye being operated on, thereby minimizing delay in eye pressure sensor readings. However, a pressure sensor that is used in a surgical handpiece can be sensitive to temperature and, thereby, is reliable when the handpiece and pressure sensor integrated therewith are at or near room temperature. As such, surgeons may need to wait for the handpiece to cool down after certain events, such as sterilization, so that the pressure sensor integrated therewith can provide stable and accurate measurements of IOP during a surgical procedure. In instances where a handpiece comprising such a pressure sensor is required to be sterilized immediately before use, having to wait for the handpiece to cool can be time consuming and affect the efficiency and throughput of procedures in the care facility.

The following description provides systems and methods that address the issues described above related to the monitoring and maintaining of IOP in a patient's eye during ophthalmic surgical procedures. Accordingly, embodiments of the present disclosure relate to the dynamic thermal compensation of thermally-induced pressure sensor drift in pressure sensors and the adjusting of fluid pressure measurements by such pressure sensors based on the temperature of the pressure sensors.

FIG. 1 illustrates an exemplary surgical system 10 for use during an ophthalmic surgical procedure, according to certain embodiments of the present disclosure. In certain embodiments, the surgical system 10 may include a surgical console 100 similar to ophthalmic surgical consoles that have been known and used, such as the CONSTELLATION® Vision System available from Alcon Laboratories, Inc. (Fort Worth, Texas) or the CENTURION® Vision System available from Alcon Laboratories, Inc. (Fort Worth, Texas), or any other ophthalmic surgical console suitable for use with the principles described herein.

As shown, the surgical console 100 may be connected to or in communication with a handpiece 118 for performing various operations of the procedure, and a foot pedal 106 that an operator may use in controlling one or more functions and/or systems of the surgical console 100. The handpiece includes a memory, such as an electrically erasable programmable read-only memory (hereafter, EEPROM 119) for storing data relating to the operation and use of the handpiece 118. Data stored in the EEPROM 119 may be retrieved and used by the surgical console 100 when the surgical console 100 is connected to or in communication with the handpiece 118. In certain embodiments, the handpiece 118 may also include a vitrectomy probe, a phacoemulsification probe, or the like. The surgical console 100 may further be connected to or in communication with an associated display 104 for displaying data relating to the operation and performance of the surgical console 100 during the ophthalmic surgical procedure. In some embodiments, display 104 may be integrated with surgical console 100. In other embodiments, display 104 may be an external display separate from surgical console 100.

Surgical console 100 may also include a computer system 108 having a central processing unit (CPU) 110, a memory 112, and a plurality of support circuit 114. The surgical console 100 may also include one or more systems and/or subsystems that may be used while performing the ophthalmic surgical procedure. For example, the surgical console 100 may include a foot pedal system 116 in communication with the foot pedal 106, a fluidics system 120 having an irrigation system 122 and an aspiration system 124, and/or an ultrasonic generator system 126. The fluidics system 120 may be used for delivering and aspirating fluid(s) to and from the eye of a patient, respectively, during the procedure using the handpiece 118. The ultrasonic generator system 126 may be used for driving an ultrasonic oscillation handpiece, such as handpiece 118, to perform phacoemulsification during a cataract procedure. The fluidics system 120 and the ultrasonic generator system 126 may thus be operably coupled with the handpiece 118. In some embodiments, the systems may overlap and cooperate to perform various aspects of a cataract surgery procedure.

Figure 2:
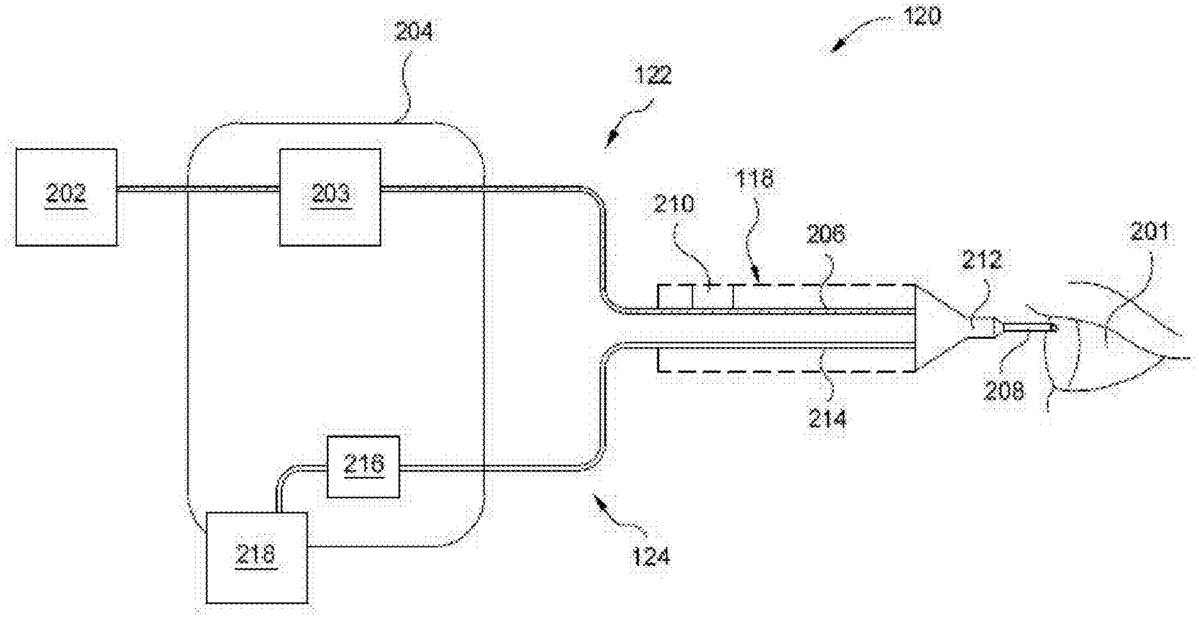
FIG. 2 is a schematic diagram of an exemplary fluidics system for use with the system of FIG. 1, according to certain embodiments of the present disclosure.

FIG. 2 is a schematic diagram of an exemplary fluidics system 120 that may be implemented with the surgical system of FIG. 1, according to certain embodiments of the present disclosure. The fluidics system 120 includes the irrigation system 122 and the aspiration system 124, each in communication with the handpiece 118. The irrigation system 122 includes an irrigation source 202, such as a sterile solution reservoir, and an irrigation valve 203 that regulates flow from the irrigation source 202 to the surgical site (labeled in FIG. 2 as an eye 201), connected by flexible tubing. The handpiece 118 includes a working tip 208 (such as a phacoemulsification tip or a vitrectomy needle). In some embodiments, an irrigation sleeve 212 may be disposed about the working tip 208

The example irrigation system 122 extends between the irrigation source 202 and the handpiece 118 and carries irrigating fluid through an irrigation flow path 206 to the surgical site during the surgical procedure. The irrigation source 202 may be a mechanically pressurized fluid source such as, for example, a clamping pressure system. In other embodiments, the irrigation source 202 may be a fluid source suspended by a pole (e.g., an IV (intravenous) pole), which may or may not be adjustable. Other fluid sources may be used. In one example, the sterile fluid is a saline fluid such as BSS; however, other fluids may be used. In some embodiments, at least a portion of the irrigation system 122 is integrated with or disposed in a surgical cassette 204 that cooperates with the surgical console 100 in FIG. 1 to provide fluid communication between the irrigation source 202 and the patient's eye 201. The pressure of the fluid in the irrigation flow path 206 may be monitored via a pressure sensor 210 in the handpiece 118 as described below.

The example aspiration system 124 includes an aspiration flow path 214 in the handpiece 118, a pump 216, and a drain or drain reservoir 218, connected by flexible tubing. As can be seen, the aspiration system 124 extends from the surgical site (eye 201) to the drain reservoir 218. The aspiration system 124, including the aspiration flow path 214, may be in fluid communication with the bore of the working tip 208 of the handpiece 118. The aspiration system 124 is used to aspirate fluid as well as any other materials to be aspirated from the eye, such as emulsified particles, through the aspiration flow path out of the eye during the surgical procedure.

In some embodiments, at least a portion of the aspiration system 124 is integrated with or disposed in surgical cassette 204 that cooperates with the surgical console 100 in FIG. 1 to provide fluid communication between the handpiece 118 and the drain reservoir 218. The drain reservoir 218 may be a bag or any suitable container, and, in some embodiments, it may be a drain instead of a self-contained reservoir.

As discussed above, to monitor the IOP of the eye during ophthalmic surgical procedures, pressure sensors may be used in the handpiece 118 to measure the pressure of fluid flowing into and out of the eye when fluid is irrigated and aspirated. Accordingly, the handpiece 118 includes a pressure sensor 210 for monitoring the pressure of fluid flowing through the irrigation flow path and/or the aspiration flow path in the handpiece 118. In some embodiments, the pressure sensor 210 comprises a pressure transducer.

In some embodiments, the pressure sensor 210 may be disposed along or operably coupled with the aspiration flow path 214 of the handpiece 118 to measure the pressure exerted by aspiration fluid in the aspiration flow path 214, thereby providing an indirect indication of the IOP in the eye. The measurement of the fluid pressure of the aspiration fluid flowing from the eye of the patient may also enable a user to better determine if any partial or total occlusions in the aspiration flow path 214 occur during a surgical procedure. In certain other embodiments, the pressure sensor 210 may be disposed along or operably coupled with the irrigation flow path 206 of the handpiece 118 to measure the pressure exerted by irrigating fluid in the irrigation flow path 206. Similar to measuring fluid pressure in the aspiration flow path 214, the measurement of the fluid pressure of the irrigating fluid flowing into the eye of the patient may enable the user to better monitor the IOP of the eye.

In further examples, it can be desirable to simultaneously or sequentially monitor the pressure of fluid being irrigated and fluid being aspirated from the patient. Thus, in some embodiments, a plurality of pressure sensors 210 may be used, wherein one or more sensors are disposed along or operably coupled with each of the aspiration flow path 214 and the irrigation flow path 206.

Certain existing pressure sensors implemented in handpieces for ophthalmic surgical procedures typically include piezo-resistive pressure sensors that utilize piezo-resistive strain gage sensing elements. Since the sensing elements in such piezo-resistive pressure sensors are sensitive to temperature, the sensors can become unstable at higher temperatures (e.g., temperature above ambient or room temperature) such that measurements obtained at higher temperatures become inaccurate and unreliable.

The systems and methods of the present disclosure resolve the problem described above by actively compensating and adjusting the working parameters and output of the pressure sensor 210 based on measured temperatures of the pressure sensor 210 (and/or the handpiece 118). In some embodiments, the temperature of the pressure sensor 210 may be measured using a temperature sensor, such as a thermistor, coupled to the pressure sensor 210 within the handpiece 118. In other embodiments, the temperature of the pressure sensor 210 may be determined indirectly by measuring and using an output impedance of the pressure sensor 210.

In some embodiments, the pressure sensor 210 as described herein enables accurate measurement of IOP of the eye 201 of the patient during an ophthalmic surgical procedure even when the handpiece 118, and thus the pressure sensor 210, has been elevated to relatively high temperatures, such as about 135° C. The present disclosure therefore provides advantages over existing pressure sensing systems used for ophthalmic surgical procedures, which do not compensate and/or adjust the working parameters of pressures sensors in response to elevated temperatures and/or temperature fluctuations.

Figure 3:
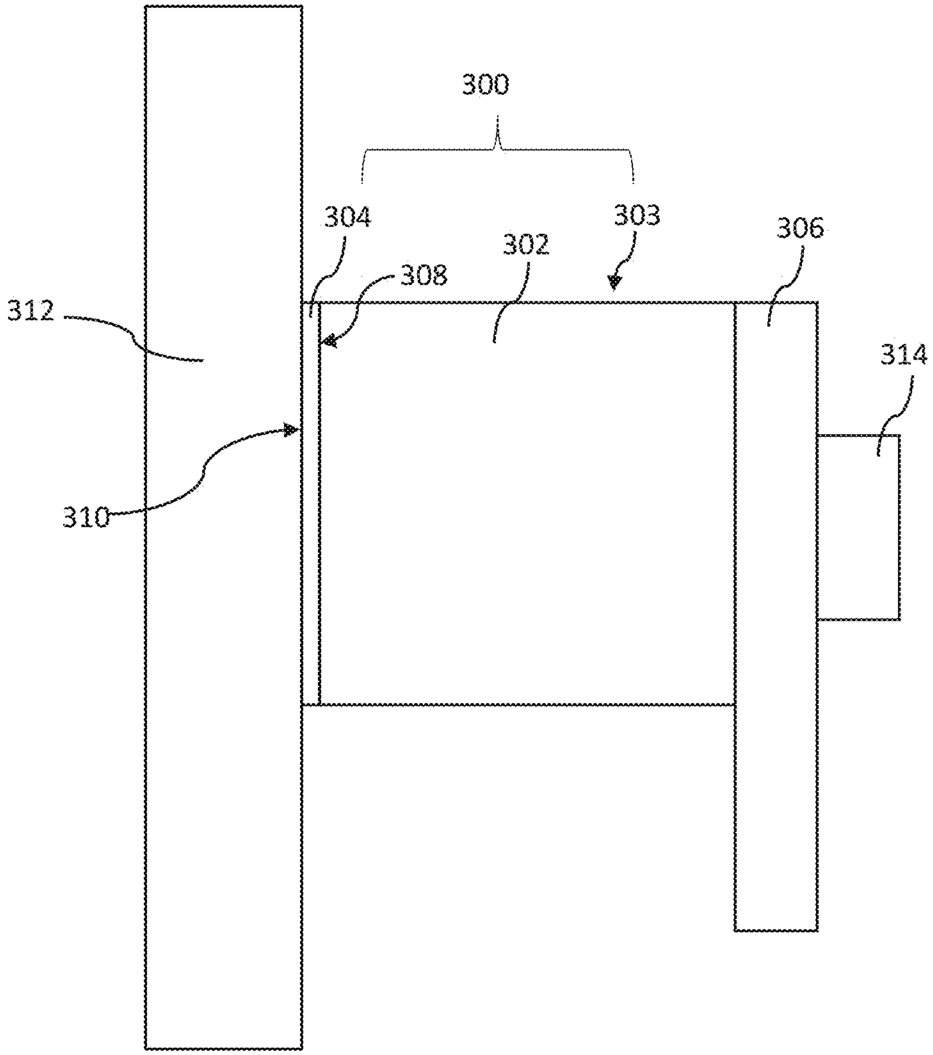
FIG. 3 is a schematic diagram of an exemplary pressure sensor that may be implemented in a handpiece of the fluidic systems in FIG. 2, according to certain embodiments of the present disclosure.

FIG. 3 is a schematic diagram of an exemplary pressure sensor 300 that may be implemented in the handpiece 118 described above, according to certain embodiments of the present disclosure. In certain embodiments, the pressure sensor 300 is representative of the pressure sensor 210 in FIG. 2.

As shown, the pressure sensor 300 includes a sensing circuit 302 integrated within a housing 303 and disposed adjacent to a flexible diaphragm 304. The pressure sensor 300 may further be connected to various supporting circuits formed on a printed circuit board (PCB) 306 adjacent to the housing 303 on the opposite side of the flexible diaphragm 304 within the handpiece 118. The flexible diaphragm 304 includes a circuit side 308 and a pressure medium side 310, with the circuit side 308 in contact with the housing 303 of the pressure sensor 300. The pressure medium side 310 of flexible diaphragm 304 may in turn face a fluid flow path 312 extending through the handpiece 118. The sensing circuit 302 of pressure sensor 300 may be electrically coupled to the circuit side 308 of the flexible diaphragm 304 for measuring pressures applied against the pressure medium side 310 from the fluid flow path 312. In some embodiments, the fluid flow path 312 may be the irrigation flow path 206 and the pressure sensor 300 may be disposed adjacent to the irrigation flow path 206 to measure the pressure of the fluid flowing through the irrigation flow path 206. In other embodiments, the fluid flow path 312 may be the aspiration flow path 214 extending through the handpiece 118, and the pressure sensor 300 may be disposed along the aspiration flow path 214 to measure the pressure of the fluid flowing through the aspiration flow path 214.

As mentioned above, the pressure sensor 300 may be used to measure the pressure applied (e.g., by fluid flow through the fluid flow path 312) against the pressure medium side 310 of the flexible diaphragm 304 using the sensing circuit 302 connected to the circuit side 308 of the flexible diaphragm 304. In some embodiments, to measure fluid pressure, the sensing circuit 302 connected to the circuit side 308 of the flexible diaphragm 304 senses deformation or displacement of the flexible diaphragm 304 as caused by the flow of fluid against the pressure medium side 310 of the flexible diaphragm 304, which is then correlated to fluid pressure by a processing unit of the fluidics system 120 and/or the computer system 108.

The pressure sensor 300 may also include a thermistor 314 operably connected to the sensing circuit 302 and/or PCB 306. In some embodiments, the thermistor 314 may be coupled to the PCB 306 on the opposite side from the sensing circuit 302 in the housing 303. The flexible diaphragm 304, sensing circuit 302, and thermistor 314 may all be electrically and operably connected. The thermistor 314 is configured to measure a temperature of the pressure sensor 300 and/or handpiece 118 when the pressure sensor 300 is measuring a pressure of the fluid flow path 312 (and/or while the handpiece 118 is in use, generally).

In some embodiments, the flexible diaphragm 304 may be a thin sheet or plate of metallic material that moves in response to forces exerted upon the flexible diaphragm 304 by fluid flowing through the fluid flow path. In some embodiments the flexible diaphragm 304 may comprise materials such as gold, silver, other biocompatible materials, and the like. As an example, the flexible diaphragm 304 may be about 5 mm (millimeters) in width, about 5 mm in length, and about 0.07 mm in thickness. However, other suitable materials that may be biocompatible, shapes, and dimensions for the flexible diaphragm 304 are also contemplated to be within the scope of the disclosure and may depend on the size of the pressure sensor 300.

In some embodiments, the flexible diaphragm 304 may be integrated with the housing 303 for the sensing circuit 302 such that the flexible diaphragm 304 is formed as one of the faces of the housing 303. In some embodiments, the pressure medium side 310 may be integrated with the fluid flow path 312 such that the pressure medium side 310 is in direct contact with the fluid flowing through the fluid flow path 312. In such an embodiment, the housing 303 may be fluidically and/or hermetically sealed such that the interior of the housing 303, including the circuit side 308 of the flexible diaphragm 304 and the sensing circuit 302, are protected from the fluid flowing through the fluid flow path 312.

Figure 4:
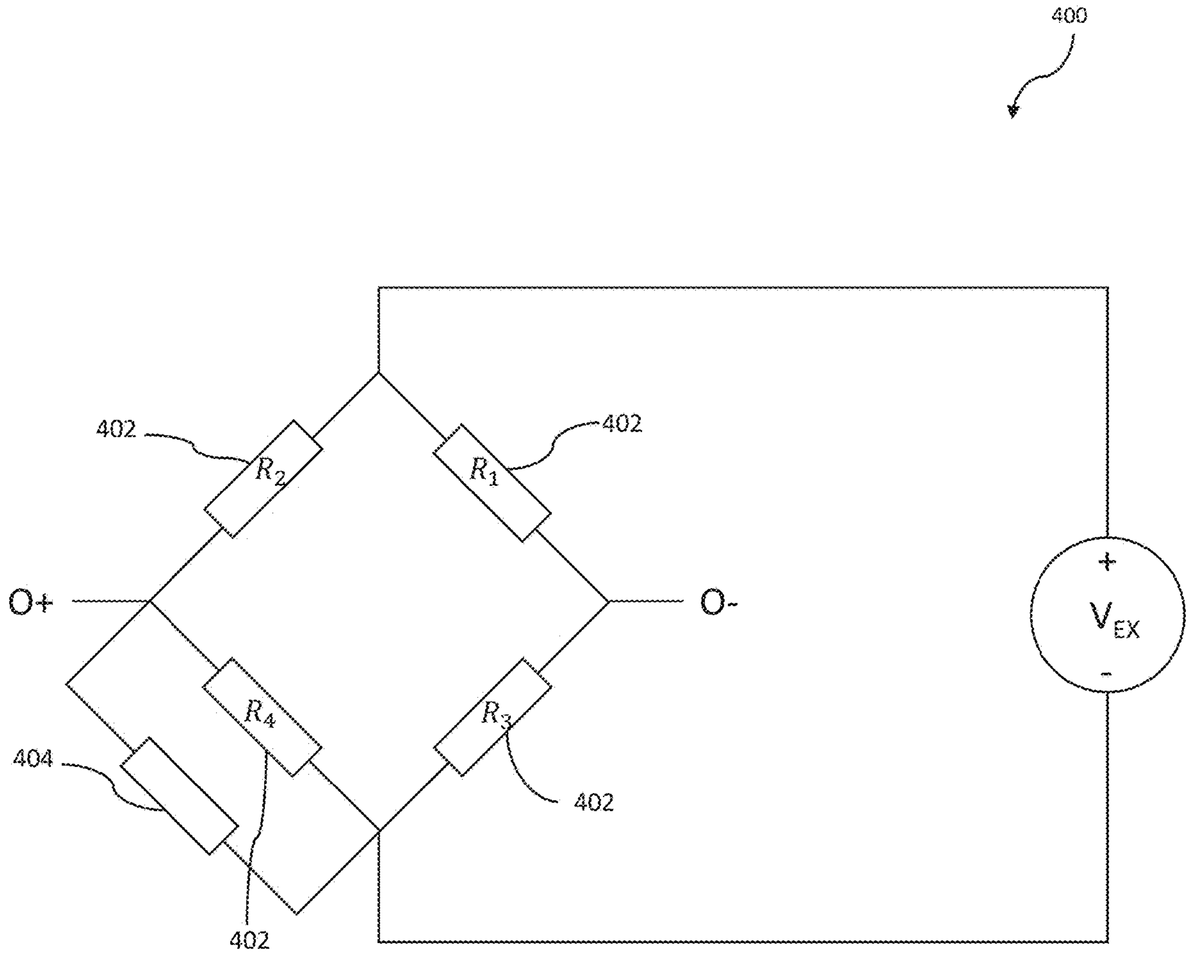
FIG. 4 is a schematic diagram of an exemplary circuit that may be implemented in the pressure sensor of FIG. 3, according to certain embodiments of the present disclosure.

FIG. 4 is a schematic diagram of an exemplary circuit 400 that may be implemented in the pressure sensor 300 of FIG. 3, according to certain embodiments of the present disclosure. In certain embodiments, the exemplary circuit 400 described in FIG. 4 is representative of the sensing circuit 302 of pressure sensor 300 in FIG. 3. As shown, the circuit 400 may include one or more strain gages 402 electrically coupled together in a Wheatstone bridge arrangement.

In some embodiments, the circuit 400 includes four strain gages 402 connected in a full-bridge strain gage Wheatstone bridge, and a shunt resistor 404. In certain embodiments, the strain gages 402 may comprise piezo-resistive strain gages made of semiconductor materials such as silicon and/or germanium. In certain other embodiments, the strain gages 402 may comprise piezo-resistive strain gages made of a length of metal wiring. The strain gages 402 may be bonded to a diaphragm of a pressure sensor, such as the flexible diaphragm 304 of pressure sensor 300. Pressure sensors with such piezo-resistive strain gages may utilize resistive or piezo-resistive effects to sense and transduce applied pressure into a measurable and standardized electrical signal. In some embodiments, piezo-resistive strain gage measurements from such pressure sensors may be obtained using the Wheatstone bridge circuit by providing an excitation voltage to the Wheatstone bridge.

When pressure is applied to a pressure sensor having the circuit 400 implemented therein, circuit 400 may utilize changes in electrical resistance of the strain gages 402 due to piezo-resistive effect, to measure the applied pressure. Specifically, the applied pressure will cause changes in resistances along the Wheatstone bridge, resulting in a corresponding output voltage, $V_0$, by the pressure sensor. The output voltage of the Wheatstone bridge in circuit 400 may be summarized with the following formula:

$$V_o = \left[\frac{R_2}{R_2 + R_4} - \frac{R_1}{R_1 + R_3}\right] \times V_{ex}$$

For example, when integrated in the pressure sensor 300, the four strain gages 402 in circuit 400 may be arranged such that pressure on the pressure medium side 310 of flexible diaphragm 304 will cause the resistance in the four strain gages 402 to change when the flexible diaphragm 304 is displaced. Accordingly, during use, application of forces by flowing fluids against the pressure medium side 310 of the flexible diaphragm 304 produces small displacements in the flexible diaphragm 304 that increases the resistance of two of the strain gages 402 and decreases the resistance in the other two strain gages 402. The change in resistance of the four strain gages 402 causes an unbalancing of the Wheatstone bridge, thereby producing an output voltage proportional to the displacement of the flexible diaphragm 304, and hence, to the pressure applied thereto by fluids flowing in the fluid flow path 312.

When there is no strain (e.g., the pressure sensor 300 is at ambient pressure with no additional applied pressure), and all the strain gages 402 in the bridge are balanced, the output from the pressure sensor 300 should ideally be zero volts. However, due to inherent imbalance between the arms of the Wheatstone bridge in circuit 400 and residual stress in each of the strain gages 402, the output from the pressure sensor 300 at ambient pressure, when there is no outside pressure or strain applied to the pressure sensor, may often not be zero. Such output from the pressure sensor 300 at ambient pressure may be defined as a “zero offset.” In certain embodiments, the zero offset at ambient pressure may be stable when the pressure sensor 300 is at or near room temperature. In this case, the zero offset may be passively compensated for during use of the pressure sensor 300 by the application of a constant that is equivalent to this initial zero offset measured at ambient pressure and room temperature.

However, it has been observed by the inventors of the present application that the residual stress of the piezo-resistive strain gages in the pressure sensor 300 are sensitive to temperature, and this sensitivity causes the zero offset of the pressure sensor 300 to shift nonlinearly with changes in temperature (of the pressure sensor 300). As such, passive compensation by application of the constant equivalent to the initial zero offset may only provide accurate IOP measurements when the pressure sensor 300 is within a limited temperature span (e.g., at or near room temperature, such as about 20° C. (Celsius)) where the initial zero offset of the pressure sensor 300 is known to be stable. In circuit 400, the shunt resistor 404 connected to the Wheatstone bridge may therefore be used to check that the span of the output from the pressure sensor 300 is within an acceptable range for passive compensation to confirm that the compensation by the initial zero offset is accurate.

In contrast, at elevated temperatures (e.g., temperatures greater than 20° C., such as up to and between about 135° C. and about 150° C.), the zero offset of the pressure sensor 300 may become unstable and change to a shifted zero offset corresponding to the elevated temperature of the pressure sensor 300. Addressing the shifted zero offset to obtain accurate IOP measurements becomes challenging, since the zero offset of the pressure sensor 300 shifts nonlinearly with changes in temperature of the pressure sensor 300. In some embodiments described herein, to compensate for zero offset in a wider temperature range, a dynamic active thermal compensation technique may be implemented to compensate for the thermally shifted zero offset at elevated temperatures. The dynamic active thermal compensation may be configured to determine and adjust the pressure output from the pressure sensor 300 with the shifted zero offset based on the real-time elevated temperature of the pressure sensor 300 when pressure measurements are being taken.

In some embodiments, active compensation techniques, alone, may be implemented in the handpiece 118. In some embodiments, both the active compensation and the passive compensation techniques discussed above may be implemented with the pressure sensor 300 to compensate for the initial and the shifted zero offset of the pressure sensor 300. As mentioned above, passive compensation using the initial zero offset may only be effective and reliable when the pressure sensor 300 is within a limited temperature range where the zero offset is stable. In contrast, active compensation of the thermally shifted zero offset based on a real-time measured temperature of the pressure sensor and a defined and/or predetermined correlation function enables the zero offset of the pressure sensor 300 to be determined and compensated for in a wider temperature range, as compared to passive compensation alone.

Figure 5:
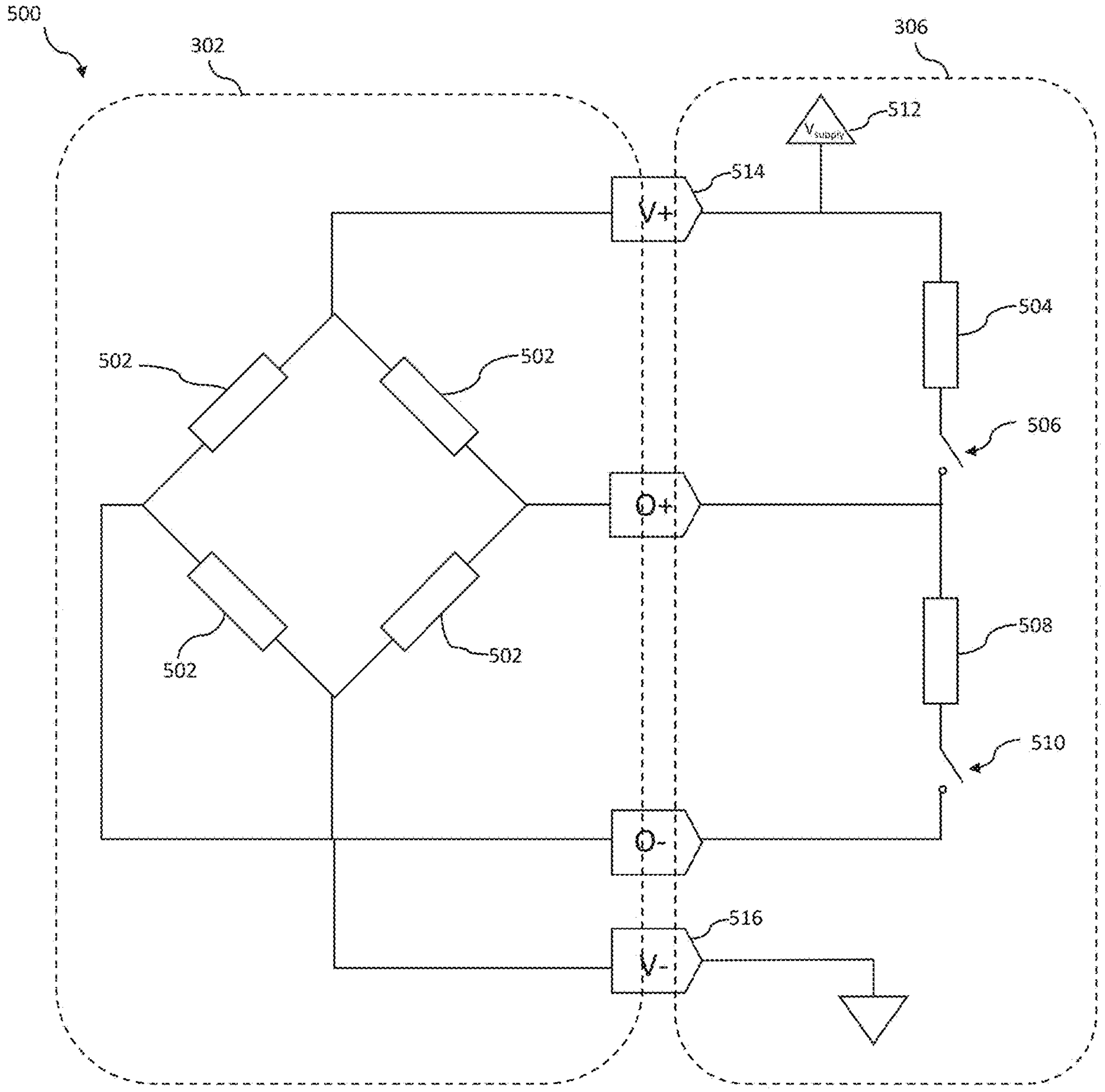
FIG. 5 is a schematic diagram of an exemplary circuit that may be implemented in the pressure sensor of FIG. 3, according to certain embodiments of the present disclosure.

FIG. 5 is a schematic diagram of another exemplary circuit 500 that may be implemented with the pressure sensor 300 of FIG. 3 and in the handpiece 118 of FIG. 1, according to certain embodiments of the present disclosure. In certain embodiments, a portion of the exemplary circuit 500 may be representative of the sensing circuit 302 implemented in pressure sensor 300 in FIG. 3. As shown, the circuit 500 includes one or more semiconductor strain gages 502 electrically connected in a Wheatstone bridge arrangement. The Wheatstone bridge arrangement in the circuit 500 may be similar to the circuit 400. The circuit 500 may therefore include the four semiconductor strain gages 502 connected in a full-bridge strain gage Wheatstone bridge.

In some embodiments, as applied to the pressure sensor 300, the Wheatstone bridge portion of the circuit 500 may be implemented as the sensing circuit 302 in housing 303. To support the capability to measure the output impedance of the pressure sensor 300, the circuit 500 also includes a shunt resistor 504, a shunt resistor switch 506, an output shunt resistor 508, and an output shunt resistor switch 510 electrically connected to the Wheatstone bridge in the sensing circuit 302. The shunt resistor switch 506 and the output shunt resistor switch 510 may be used to connect and disconnect the shunt resistor 504 and the output shunt resistor 508, respectively, to and from the circuit 500. In some embodiments, as applied to the pressure sensor 300 in handpiece 118, the shunt resistor 504, shunt resistor switch 506, output shunt resistor 508, and output shunt resistor switch 510, and the connection points 514, 516 for the Wheatstone bridge excitation voltage may be formed on the PCB 306 adjacent to the pressure sensor 300 and connected to the sensing circuit 302 and voltage supply 512. In certain other embodiments, one or more of the shunt resistors and switches, such as the shunt resistor 504, shunt resistor switch 506, output shunt resistor 508, and output shunt resistor switch 510, may alternatively be implemented in the surgical console 100.

In pressure sensors utilizing piezo-resistive semiconductor strain gages, such as circuit 500 as implemented in pressure sensor 300, it was observed that output impedance (also known as the output resistance) of the Wheatstone bridge in circuit 500 changes linearly with the temperature of the pressure sensor 300 but is independent of the pressure that the pressure sensor is exposed to. In such embodiments, the temperature of the pressure sensor 300 may therefore be obtained from the output impedance of the circuit 500 at various pressures using a determined linear temperature correlation constant.

To determine an output impedance of the pressure sensor 300, the shunt resistor switch 506 can be used to close circuit 500 with respect to the shunt resistor 504, thereby enabling current to flow through shunt resistor switch 506 and providing a first shunt configuration of the circuit 500 (e.g., where circuit 500 is complete with respect to shunt resistor 504 but not output shunt resistor 508). With the circuit 500 closed with respect to shunt resistor 504, the output shunt resistor switch 510 can used to close circuit 500 with respect to the output shunt resistor, thereby enabling current to also flow through the output shunt resistor 508 and providing a second shunt configuration in the circuit 500 (e.g., where circuit 500 is complete with respect to both shunt resistor 504 and output shunt resistor 508). Together, the two different shunt configurations enabled by the shunt resistor 504 and output shunt resistor 508 may be used to provide two voltage samples in the circuit 500 to determine the output impedance of the pressure sensor 300 when the pressure sensor 300 is used to measure/monitor a pressure.

In some embodiments, the output impedance of the circuit 500 may be calculated using the following equation and applying Ohm's law thereto:

$$R_{Sensor\ Output\ Impedance} = \frac{(V_{Shunt} - V_{Output\ Shunt})}{V_{Output\ Shunt}} \times R_{Output}$$

wherein:

$V_{Shunt}$ is the output voltage, $V_{Sensor}$, when $R_{Shunt}$ is applied;

$V_{Output\ Shunt}$ is the output voltage, $V_{Sensor}$, when both $R_{Shunt}$ and $R_{Output\ Shunt}$ are applied; and $R_{Output}$ is about 1.5 kΩ, the resistance of the output shunt resistor.

The shunt resistor 504 is applied in both voltage samples ($V_{Shunt}$ and $V_{Output\ Shunt}$) to induce a non-zero voltage across the output of the pressure sensor 300, thereby enabling the determination of the output impedance $R_{Sensor\ Output\ Impedance}$ using the above equation. The output impedance of the circuit 500 may thereafter be used to determine the corresponding temperature of the pressure sensor 300 using the linear temperature correlation function between the output impedance and temperature of the pressure sensor 300 in the handpiece 118.

In some embodiments, the thermistor 314 may be used to determine the temperature of the pressure sensor 300. In other embodiments, the thermistor 314 may be used as a check, or confirmation, on the temperature of the pressure sensor 300 as determined from the output impedance of the pressure sensor 300 as discussed above. In some embodiments, the thermistor 314 may be a temperature-dependent resistor electrically connected to the sensing circuit 302 in the pressure sensor 300. Changes in temperature of the pressure sensor 300 may either increase or decrease the resistance of the thermistor 314. As such, a linear temperature correlation function/equation based on the output of the thermistor 314 may also be used to determine the temperature of the pressure sensor 300.

As discussed above, the residual stress of the piezo-resistive strain gages in the sensing circuit 302 of pressure sensor 300 are sensitive to temperature and shift nonlinearly with changes in the temperature of the pressure sensor 300. However, a zero-offset correlation between the zero offset and the temperature of the pressure sensor 300 may be established by sampling the output pressure and the output impedance of the pressure sensor 300, with no pressure applied thereto, at various temperatures as the temperature of the pressure sensor 300 changes. In some embodiments, the sampling measurements to establish the zero offset correlation may be obtained from the pressure sensor 300 as the pressure sensor 300 is heated (e.g., to a sterilization temperature such as 135° C.). In other embodiments, the sampling measurements may be obtained while the pressure sensor 300 is cooled.

In some embodiments, if the pressure sensor 300 otherwise includes parameters that are not a function of temperature (e.g., thermal conductivity, specific heat), the zero-offset correlation from sampling the pressure sensor 300 during cooling and/or heating may be the same. In such embodiments, only a single sampling may need to be conducted to establish the zero-offset correlation that may be used for both instances where the pressure sensor 300 is being heated or cooled during use. In other embodiments, if the pressure sensor 300 includes working parameters and or material properties that vary as a function of temperature, the correlation derived between sampling periods during heating and cooling of the sensor may be different. In such instances, sampling periods for both heating and cooling of the pressure sensor 300 may need to be conducted to establish correlations for each instance.

When sampling the pressure sensor 300 to establish the zero offset correlation thereof, the corresponding output voltage and output impedance of the pressure sensor 300 is measured and recorded as the temperature of the pressure sensor 300 changes. As mentioned above, the output voltage measured from the pressure sensor 300 may be used to determine the pressure applied to the pressure sensor 300. However, since no pressure is actually applied to the pressure sensor 300 during the sampling period, the output pressure determined with the measured output voltage may therefore correspond to the thermally-shifted zero offset of the pressure sensor 300 for the specific temperature of the pressure sensor 300 when the sample measurement is taken. The corresponding temperature of the pressure sensor 300 for each thermally-shifted zero offset recorded may be determined by subsequently measuring the output impedance of the pressure sensor 300. Since the output impedance of the pressure sensor 300 linearly corresponds with the temperature of the pressure sensor 300, the zero offset correlation may be established by using either the sampled output impedance or the corresponding temperature of the pressure sensor 300.

As mentioned above, during the sampling period for establishing the zero-offset correlation, the output voltage and output impedance of the pressure sensor may be measured and recorded in alternating samples so as to obtain and collect corresponding output voltage measurement and output impedance measurement for specific/individual temperatures of the pressure sensor 300 as the temperature of the pressure sensor 300 changes. For example, the output voltage of the pressure sensor 300 may be recorded in a first sample. In the subsequent sample, the corresponding output impedance may in turn be obtained with the assumption that no change in the corresponding output voltage has occurred. The assumption enables the temperature of the pressure sensor 300, determined from the subsequently measured output impedance, to correspond with the thermally shifted zero offset determined from the output voltage measured in the prior sample. The sample period may therefore include alternating measurements of the output voltage and output impedance from the sensing circuit 302 in the pressure sensor 300 as the temperature of the pressure sensor 300 changes.

In some embodiments, the time between voltage and impedance measurements is sufficiently short (e.g., in a scale of sub-seconds or less than a second) to ensure that changes in the corresponding output voltage or output impedance measurements are negligible to support the assumption described above being made during sampling. In some embodiments, during the sample period in which output impedance is measured, an additional offset may also be introduced to increase the signal to noise ratio to minimize recording output impedance samples having a corresponding 0 output voltage.

Once sampling of the pressure sensor 300 is complete, a zero offset correlation function for the pressure sensor 300 may be derived from the sampling measurements of the thermally-shifted zero offsets and the output impedance by fitting the sampled data to a mathematical correlation curve. The mathematical correlation function may include any order polynomial that fits the sampled data. In some embodiments, the correlation curve may be represented by a third order polynomial function in the form of $f(t)=at^3+bt^2+ct+d$ where f(t) is the zero-offset calculated as a function of temperature t determined from the output impedance of the pressure sensor 300. The zero offset correlation function derived from the fitted curve for the sampled measurements of the pressure sensor 300 may then be used to predict the thermally-shifted zero offset of the pressure sensor 300 at a specific temperature within the sampled range when the pressure sensor 300 is in use. Using the zero offset correlation function therefore enables a user to dynamically compensate for the output pressure measured by the pressure sensor 300 with the thermally-shifted zero offset to ensure accurate IOP measurements at elevated temperatures.

Since the configuration of pressure sensors may vary from handpiece to handpiece, the zero offset correlation discussed above may be specific to the pressure sensor 300 and its environment (e.g., the specifics of the handpiece 118 that the pressure sensor 300 may be implemented in). As such, in certain embodiments, sampling of each handpiece 118 and the pressure sensor 300 therein may be required to establish the zero offset correlation curve and corresponding function for each individual handpiece 118 and pressure sensor 300 integrated therewith on a case-by-case basis. The sampling may be performed prior to the utilization of each of the handpiece 118 and the pressure sensor 300 therein. For example, during manufacturing, each handpiece 118 and/or pressure sensor 300 integrated therewith may be individually calibrated during a calibration cycle where the handpiece 118 and/or pressure sensor 300 are heated and then allowed to cool to room temperature. During the calibration cycle, the output voltage, output impedance, thermistor, and zero offset data may be collected, as necessary, to determine a corresponding zero offset correlation function for the specific handpiece 118 and pressure sensor 300.

In certain embodiments, a check may be performed on how well the sampled data fits the polynomial function by calculating and checking the R-squared value of the function. The R-squared value may be computed using standard statistical polynomial regression analysis. The polynomial function may be considered acceptable for use if the R-squared value is above a predetermined threshold. For example, an R-squared value of 0.95 is considered statistically passing, meaning the error between the actual device and calculated curve is acceptable, and may therefore be sufficient. If the R-squared value is below the predetermined threshold, then additional sampling of the specific handpiece 118 and the pressure sensor 300 therein may need to be conducted and a new polynomial function for the zero offset correlation curve generated until the R-squared value is at an acceptable value.

In certain embodiments, an additional check on the acceptability of a generated zero-offset correlation curve/derived function may be performed by assessing the difference between the maximum and minimum zero offset shifts during the sampled period. If the difference is under a predetermined threshold (e.g., for example ≤5 mmHg (millimeters of Mercury)), the zero-offset correlation generated for the specific handpiece 118 and the pressure sensor 300 therein may be considered sufficient. In such circumstances, even if sampled data for the calibrated pressure sensor 300 fails to meet the above-mentioned R-square criterion, the generated zero-offset correlation may none the less be acceptable since the thermal shift is sufficiently low and may still meet the performance requirement of the pressure sensor 300 in the handpiece 118.

In certain embodiments, the zero offset correlation function established for each pressure sensor 300 may be programmed and stored in the EEPROM 119 (Electrically erasable programmable read-only memory) of the handpiece 118. In some embodiments, the zero offset correlation function may be recorded in the EEPROM 119 in the form of cubic function coefficients. When the handpiece 118 is in use, the handpiece 118 is in communication (via wired or wireless connection) with the surgical console 100 such that the zero offset correlation function may be retrieved by the surgical console 100 from the EEPROM 119 of the handpiece 118 each time the handpiece 118 (and thus, pressure sensor 300) is in use. In other embodiments, more than one correlation function may be determined and stored in the EEPROM 119 of the handpiece 118 for use under specific circumstances (e.g., different correlations for heating and cooling of the pressure sensor 300).

In further embodiments, one or more performance parameters related to the zero offset correlation curve of the pressure sensor 300 may be gathered and recorded in the EEPROM 119 after the handpiece 118 and the pressure sensor 300 therein is put in service. Each time the pressure sensor 300 is used, data related to the performance parameters of the pressure sensor 300 (e.g., zero offset, output impedance) may be gathered and written to the EEPROM 119 of the handpiece 118 to refine and update the programmed zero-offset correlation throughout the service life of the pressure sensor 300. In some embodiments, the output impedance of the pressure 300, which is utilized to determine sensor temperature, may shift as the pressure sensor 300 ages, thereby causing an additional zero offset shift due to the sensor aging. In such instances, the output impedance may be calibrated against temperature measurements from the thermistor 314, which may not be affected by the aging of the pressure sensor 300. The calibration value for the output impedance may then be applied to all subsequent output impedance measurements to offset the additional zero offset shift due to sensor aging. The continuous gathering of such performance and calibration parameters after every use may enable continuous accurate predictions and measurements concerning the performance of the pressure sensor 300 as the pressure sensor 300 ages. In some embodiments, such predictions may also be used in providing notifications to the user on when the pressure sensor 300 may be nearing or has reached the end of its service life in providing reliable measurements.

Figure 6:
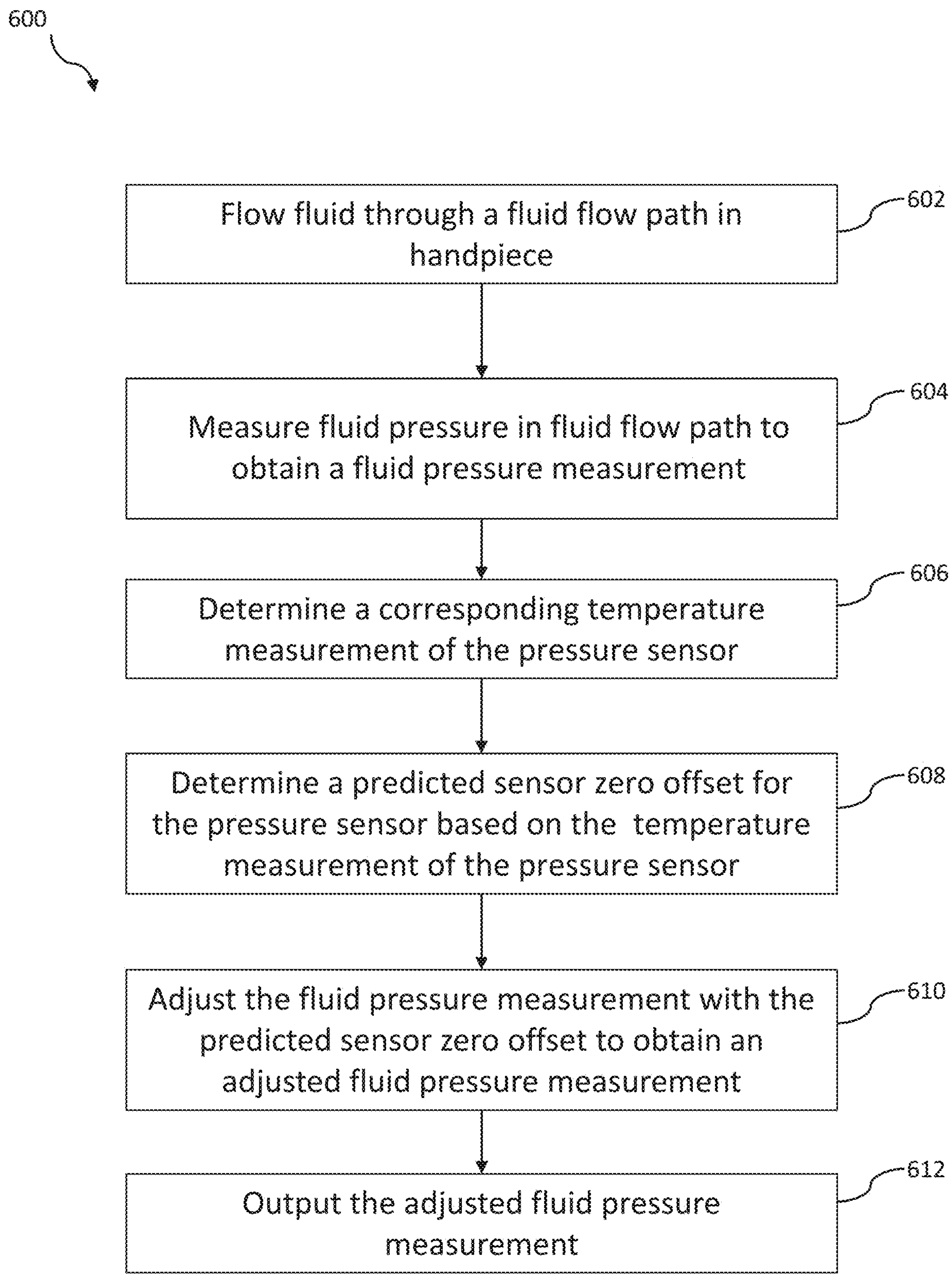
FIG. 6 is a flow diagram of an exemplary method for measuring IOP in an eye of a patient, according to certain embodiments of the present disclosure.

FIG. 6 is a flow diagram of an exemplary method 600 for measuring IOP in an eye of a patient, according to certain embodiments of the present disclosure. The method 600 may be performed by surgical system 10 and handpiece 118.

The method 600 begins, at operation 602, with the surgical system 10, flowing fluid through the fluid flow path 312 of handpiece 118, which may have a working tip disposed in the intraocular space of the patient's eye. For example, the surgical console 100, which operates handpiece 118, may cause fluid to be flown through the fluid flow path 312, in response to, for example, user input through foot pedal 106. The fluid flowing through the fluid flow path 312 may comprise fluid being irrigated into the eye of the patient or fluid being aspirated from the eye during, for example, a cataract surgery or the like.

At operation 604, the surgical system 10 measures fluid pressure in the fluid flow path 312, resulting in a fluid pressure measurement. For example, a pressure sensor (e.g., pressure sensor 210 disposed in the handpiece 118 and adjacent to the fluid flow path 312), measures the fluid pressure in the fluid flow path 312. The fluid pressure measurement may then be obtained by or communicated to computer system 108 for use in operation 610.

At operation 606, the surgical system 10 determines a corresponding temperature of the pressure sensor 210 and/or handpiece 118 simultaneously with or sequentially after the obtaining the fluid pressure measurement at operation 604. For example, computer system 108 of surgical control 100 determines an output impedance of the pressure sensor 210 when the pressure sensor 210 is used to measure the fluid pressure at operation 604 (e.g., as discussed above with reference to determining the output impedance from circuit 500 of pressure sensor 300), retrieves a determined linear temperature correlation constant from the EEPROM 119 of the handpiece 118, and applies the determined linear temperature correlation constant to the output impedance of the pressure sensor 210 to determine the temperature of the pressure sensor 210. Alternatively, as described above, a thermistor (e.g., thermistor 314 coupled to the pressure sensor 300 in the handpiece 118) in the handpiece 118 may determine the temperature of the pressure sensor 210 and/or handpiece 118. The determined temperature from the thermistor may then be obtained by or communicated to computer system 108 for use in operations 608-610.

At operation 608, the surgical system 10 determines a predicted sensor zero offset for the pressure sensor 210 based on the temperature measurement of the pressure sensor 210 obtained at operation 606. For example, computer system 108 of surgical console 100 may retrieve a predetermined zero offset correlation function from the EEPROM 119 of the handpiece 118 and use it along with the determined temperature at operation 606 to determine the predicted sensor zero offset for adjusting the fluid pressure measurement obtained at operation 604, as described below.

In certain embodiments, the predetermined zero offset correlation function may be stored in surgical console 100, such as in memory 112 of computer system 108. For example, memory 112 may store various handpiece profiles and, depending on which handpiece is being used, the corresponding profile may be used which may include the predetermined zero offset correlation function for that specific handpiece.

At operation 610, the surgical system 10 adjusts the fluid pressure measurement obtained at operation 604 using the predicted sensor zero offset determined at operation 608 to obtain an adjusted fluid pressure measurement. For example, computer system 108 of surgical console 100 performs the adjustment (i.e., calibration) discussed above.

At operation 612, the surgical system 10 may output the adjusted fluid pressure measurement to a user, such as by displaying the adjusted fluid pressure on the display 104 of surgical system 10. For example, computer system 108 of surgical console 100 may cause the adjusted fluid pressure measurement to be displayed on display 104.

Figure 7:
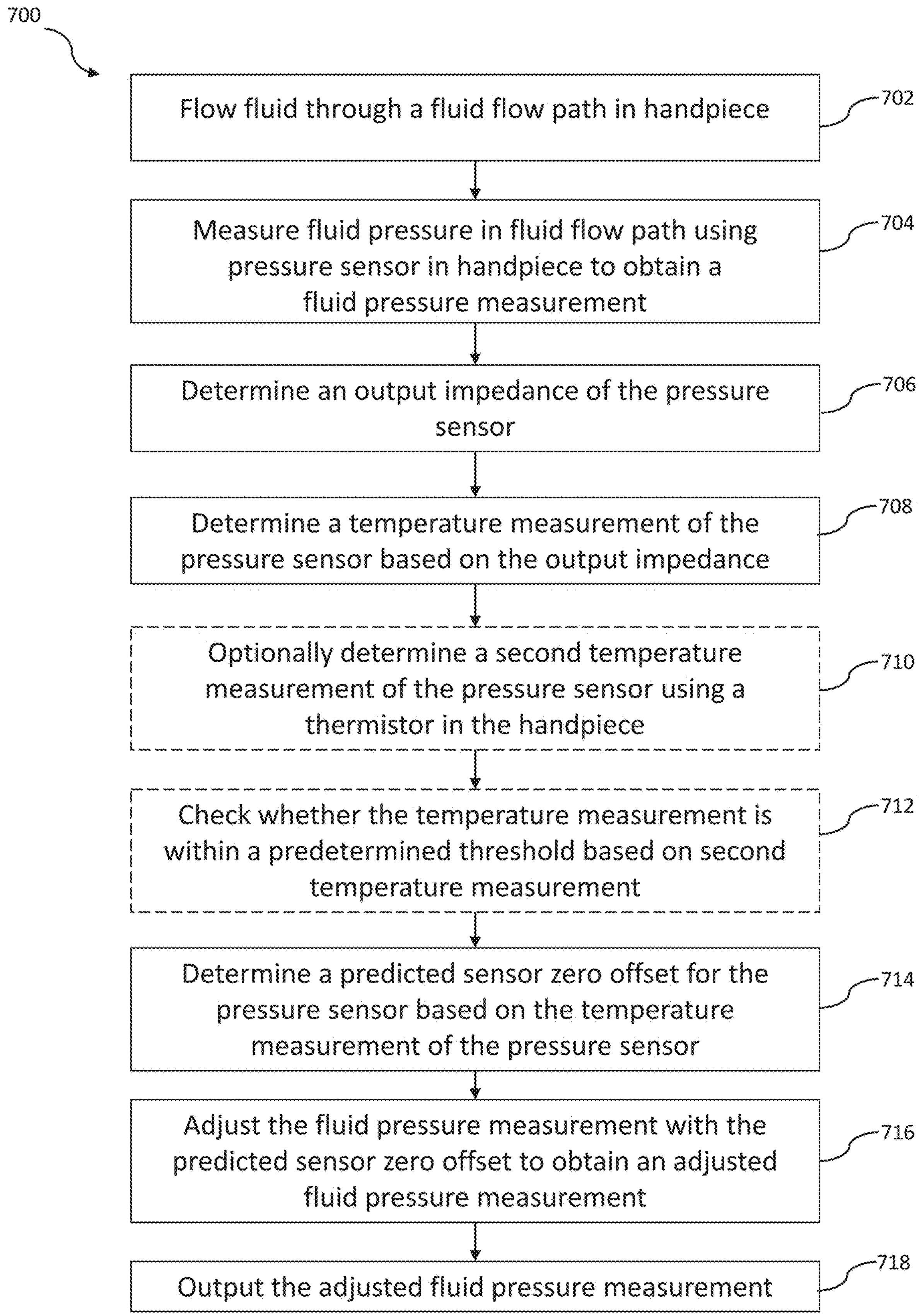
FIG. 7 is a flow diagram of an exemplary method for measuring IOP in an eye of a patient, according to certain embodiments of the present disclosure.

FIG. 7 is a flow diagram of an exemplary method 700 for measuring IOP in an eye of a patient, according to certain embodiments of the present disclosure. The method 700 may be performed by surgical system 10.

The method 700 begins, at operation 702, with the surgical system 10, flowing fluid through the fluid flow path 312 of handpiece 118, which may have a working tip disposed in an intraocular space of the patient's eye. As discussed above, the surgical console 100, which operates handpiece 118, may cause fluid to be flown through the fluid flow path 312, in response to, for example, user input through foot pedal 106. The fluid flowing through the fluid flow path 312 may comprise fluid being irrigated into the eye of the patient or fluid being aspirated from the eye during, for example, a cataract surgery or the like.

At operation 704, the surgical system 10 measures fluid pressure in the fluid flow path 312, resulting in a fluid pressure measurement. For example, a pressure sensor (e.g., pressure sensor 210 disposed in the handpiece 118 and adjacent to the fluid flow path 312), measures the fluid pressure in the fluid flow path 312. The fluid pressure measurement may then be obtained by or communicated to computer system 108 for use in operation 716.

At operation 706, the surgical system 10 determines an output impedance of the pressure sensor 210 simultaneously with or sequentially after the fluid pressure measurement performed at operation 704. For example, as discussed above, computer system 108 of surgical control 100 determines an output impedance of circuit 500 in pressure sensor 300 while the pressure sensor 300 is used to measure the fluid pressure measurement at operation 704.

At operation 708, the surgical system 10 determines a corresponding temperature measurement of the pressure sensor 210 and/or handpiece 118 using the output impedance of the pressure sensor 210 determined in operation 706. For example, computer system 108 of surgical control 100 retrieves a determined linear temperature correlation constant from the EEPROM 119 of the handpiece 118 and applies the constant to the output impedance of the pressure sensor 210 determined at operation 706 to determine the temperature measurement of the pressure sensor 210. In certain embodiments, the constant may be stored in surgical console 100, such as in memory 112 of computer system 108. For example, memory 112 may store various handpiece profiles and, depending on which handpiece is being used, the corresponding profile may be used which may include the constant for that specific handpiece.

At operation 710, the surgical system 10 may optionally determine a second temperature measurement of the pressure sensor 210 and/or handpiece 118 using a thermistor (e.g., thermistor 314 coupled to the pressure sensor 210 in the handpiece 118) in the handpiece 118. The second temperature measurement may then be obtained by or communicated to computer system 108 for use in operation 712.

If the second temperature measurement is obtained at operation 710, the method continues to operation 712 in which the surgical system 10 checks whether the temperature measurement of the pressure sensor 210 determined using the output impedance of the pressure sensor 210 at operation 708 is within a predetermined threshold (e.g., ±1-2° C.) of the second temperature measurement determined in operation 710. For example, the computer system 108 of surgical control 100 determines whether a difference between the temperature measurement determined at operation 708 and the second temperature measurement obtained at operation 710 is within the predetermined threshold. The predetermined threshold may be stored in the memory 112 of computer system 108 and used by the computer system 108 when performing operation 712.

Operations 710 and 712 may be performed by the surgical system 10 to confirm the accuracy of the temperature measurement determined from the output impedance of the pressure sensor 210 at operation 708. The predetermined threshold used when checking the temperature measurement of the pressure sensor 210 determined at operation 708 accounts for an expected tolerance, since a slight difference in measurement may be expected due to the differences in the positioning of the pressure sensor 210 and the thermistor within the handpiece 118.

If the surgical system 10 determines the temperature measurement from the output impedance of the pressure sensor 210 at operation 708 is within the predetermined threshold at operation 712, the surgical system 10 determines the temperature measurement of the pressure sensor 210 determined in operation 708 to be acceptable and the method 700 proceeds to operation 714.

In certain embodiments, if the surgical system 10 determines the temperature measurement determined from the output impedance of the pressure sensor 210 at operation 708 is not within the predetermined threshold, then operations 706 and 708 may be repeated. For example, the surgical system 10 determines a new output impedance at operation 706 and a new temperature measurement at operation 708 based on the new output impedance and compares the two at operation 712.

In certain other embodiments, if the surgical system 10 determines the temperature measurement determined from the output impedance of the pressure sensor 210 at operation 708 is not within the predetermined threshold in operation 712, the surgical system 10 may adjust the output impedance determined at operation 706 based on the difference between the temperature determined at operation 708 and the second temperature at operation 710. For example, computer system 108 of surgical console 100 performs the adjustment (i.e., correction) discussed above. If such an adjustment to the temperature measurement determined at operation 706 is made, computer system 108 of surgical console 100 determines an adjusted temperature measurement of the pressure sensor 210 using the adjusted output impedance of the pressure sensor 210.

At operation 714, the surgical system 10 determines a predicted sensor zero offset for the pressure sensor 210 based on the temperature measurement of the pressure sensor 210 determined in operation 708 or the adjusted temperature measurement of the pressure sensor 210 from operation 712, if one is determined. For example, computer system 108 of surgical console 100 may retrieve a predetermined zero offset correlation curve from the EEPROM 119 of the handpiece 118 and use it along with the aforementioned temperature measurement or adjusted temperature measurement to determine the predicted sensor zero offset for adjusting the fluid pressure measurement obtained at operation 704, as described below.

At operation 716, the surgical system 10 adjusts the fluid pressure measurement obtained at operation 704 using the predicted sensor zero offset determined at operation 714 to obtain an adjusted fluid pressure measurement. For example, computer system 108 of surgical console 100 performs the adjustment (i.e., calibration) discussed above.

At operation 718, the surgical system 10 may output the adjusted fluid pressure measurement to a user, such as by displaying the adjusted fluid pressure measurement on the display 104 of surgical system 10. For example, computer system 108 of surgical console 100 may cause the adjusted fluid pressure measurement to be displayed on display 104 connected to surgical console 100.

Figure 8:
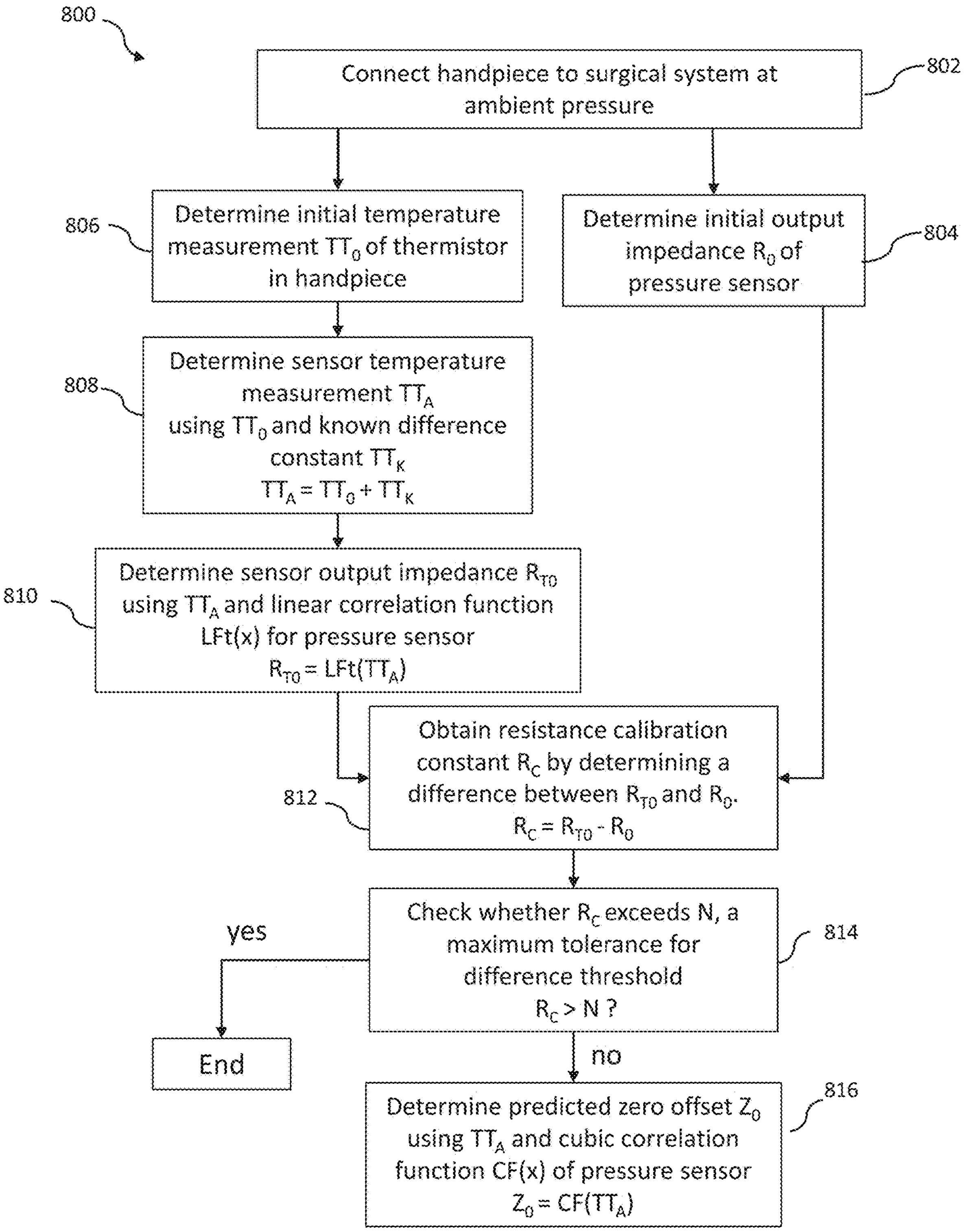
FIG. 8 is a flow diagram of an exemplary process for calibrating and determining a resistance calibration constant for the pressure sensor of FIG. 3 to compensate for age-induced zero offset shifts, according to certain embodiments of the present disclosure.

FIG. 8 is a flow diagram of an exemplary process 800 for checking and generating a resistance calibration constant for the output impedance of a pressure sensor, such as pressure sensor 300, according to certain embodiments of the present disclosure. Process 800 may be performed by surgical system 10 to compensate for age-induced zero offset shift.

In some embodiments, process 800 utilizes a previously determined and fixed difference constant, $TT_K$, between sensor temperature measurements and thermistor temperature measurements (e.g., fixed difference due to proximity of thermistor from the pressure sensor), a determined linear correlation function, LFt(x), between the sensor temperature measurement and the output impedance of the pressure senor 300, and a determined cubic correlation function, CF(x), between the sensor zero offset and the sensor temperature measurement, to check and, in some examples, calibrate the pressure sensor 300. In certain embodiments, the difference constant $TT_K$, determined linear correlation function LFt(x), and determined cubic correlation function, CF(x), may all be stored in the EEPROM 119 of the corresponding handpiece 118 and retrieved by computer system 108 for use by the surgical system 10 when the handpiece 118 is connected to surgical system 10 and process 800 is performed. Additionally or alternatively, the difference constant $TT_K$, determined linear correlation function LFt(x), and determined cubic correlation function, CF(x), may be stored in memory 112 of computer system 108.

Process 800 begins at operation 802 with connecting handpiece 118 to the surgical system 10 to activate the handpiece 118 when handpiece 118 is at ambient pressure. In certain embodiments, the handpiece 118 may also be at an elevated handpiece temperature due to the handpiece 118 being sterilized prior to use and connection to the surgical system 10 at operation 802.

Once the handpiece 118 is connected to the surgical system 10, surgical system 10 may perform operations 804-816 prior to utilization of the handpiece 118 and/or the pressure sensor 300 for a surgical procedure. Surgical system 10 performs operations 804-816 to generate and check whether the resistance calibration constant, $R_C$, of the pressure sensor 300 exceeds a predetermined tolerance threshold, N, which is the threshold for changes in the output impedance of the pressure sensor due to the aging of the pressure sensor 300. As discussed above, in some embodiments, the output impedance of the pressure sensor 300 may shift due to aging of the pressure sensor 300. Specifically, aging of the pressure sensor 300 may in turn cause the output impedance, $R_0$, of the pressure sensor 300 to increase, while the sensor temperature from the thermistor, $R_{T0}$, remains roughly unchanged.

The resistance calibration constant $R_C$ for the pressure sensor 300 corresponds to the difference between an initial output impedance, $R_0$, of the pressure sensor 300 at ambient pressure and the output impedance, $R_{T0}$ of the pressure sensor 300 determined based on the sensor temperature determined using the thermistor. In some embodiments, if $R_C$ exists but does not exceed N, then $R_C$ may be used as a calibration constant for the pressure sensor 300 to compensate for the age-induced shift in output impedance measurements. However, if $R_C$ exceeds N, surgical system 10 determines that the pressure sensor 300 may not provide reliable measurements and take one or more restricting or notifying actions to minimize risks. For example, surgical system 10 may prevent the handpiece 118 and/or pressure sensor therein from being used altogether, notify the user of the handpiece 118 of the failed calibration of the pressure sensor 300, and/or take certain appropriate actions to enable the handpiece 118 and systems connected therewith via the surgical system 10 to be only used in a "safe mode" to minimize potential risks.

At operation 804, the surgical system 10 determines the initial output impedance, $R_0$, of the pressure sensor 300 at ambient pressure. For example, computer system 108 of surgical control 100 determines an output impedance of the pressure sensor 300 (e.g., as discussed above with reference to determining the output impedance from circuit 500 of pressure sensor 300) when pressure sensor 300 is at ambient pressure with no additional pressure applied.

At operation 806, the surgical system 10 obtains the initial temperature measurement, $TT_0$, of the pressure sensor 300 using a thermistor in the handpiece 118. For example, a thermistor (e.g., thermistor 314 coupled to the pressure sensor 300 in the handpiece 118) in the handpiece 118 determines the $TT_0$ of the pressure sensor 300 and/or handpiece 118. $TT_0$ measured by the thermistor may then be obtained by or communicated to computer system 108 for use in operation 808.

At operation 808, the surgical system 10 adjusts the initial temperature measurement $TT_0$ obtained in operation 806 using a difference constant, $TT_K$, to determine a sensor temperature measurement, $TT_A$. For example, computer system 108 of surgical console 100 may retrieve $TT_K$ stored in the EEPROM 119 of the handpiece 118 and use it with $TT_0$ to perform the adjustment discussed above, based on the following function: $TT_A=TT_0+TT_K$.

At operation 810, the surgical system 10 determines a sensor output impedance, $R_{T0}$, based on the sensor temperature measurement $TT_A$ obtained at operation 808. For example, computer system 108 of surgical console 100 may retrieve the linear correlation function LFt(x) from the EEPROM 119 of the handpiece 118 and use it along with $TT_A$ to determine $R_{T0}$, in the following function: $R_{T0}=LFt(TT_A)$.

At operation 812, the surgical system 10 determines a resistance calibration constant, $R_C$, for the pressure sensor 300 based on a difference between the initial output impedance $R_0$ determined in operation 804 and the sensor output impedance $R_{T0}$ determined in operation 810. For example, computer system 108 of surgical console 100 may perform the determination discussed above to obtain $R_C$ using the following function: $R_C=R_{T0}-R_0$.

At operation 814, the surgical system 10 checks the aging of the pressure sensor 300 by comparing whether the resistance calibration constant $R_C$ obtained in operation 812 exceeds a maximum tolerance for difference threshold, N. For example, computer system 108 of surgical console 100 may retrieve N from the EEPROM 119 of the handpiece 118 and use it along with $R_C$, as obtained in operation 812, to make the determination above. In some embodiments, the maximum tolerance for difference threshold N is about 200 Ohms.

If the surgical system 10 determines $R_C$ to be less than N at operation 814, the surgical system 10 determines the handpiece 118 and pressure sensor 300 to be usable despite the resistance calibration constant $R_C$ needing to be implemented and the process 800 may proceed to operation 816.

If the surgical system 10 determines $R_C$ to be greater than N, the surgical system 10 determines that the pressure sensor 300 may not provide reliable measurements and may take any one of the aforementioned actions including notifying the user of the failed calibration of the pressure sensor 300.

At operation 816, the surgical system 10 determines a predicted zero offset, $Z_0$, for the pressure sensor 210 based on the sensor temperature measurement $TT_A$ determined in operation 808. For example, computer system 108 of surgical console 100 may retrieve a cubic correlation function CF(x) stored in the EEPROM of the handpiece 118 and use it along with $TT_A$ to determine $Z_0$, based on following function: $Z_0=CF(TT_A)$. Surgical system 10 may then apply $Z_0$ to subsequent pressure measurements from the pressure sensor 300 when the handpiece 118 and/or the pressure sensor 300 is at the elevated temperature $TT_A$ and used to measure IOP, so as to adjust the pressure measurements from the pressure sensor 300 to compensate for zero offset shifts due to temperature.

Figure 9:
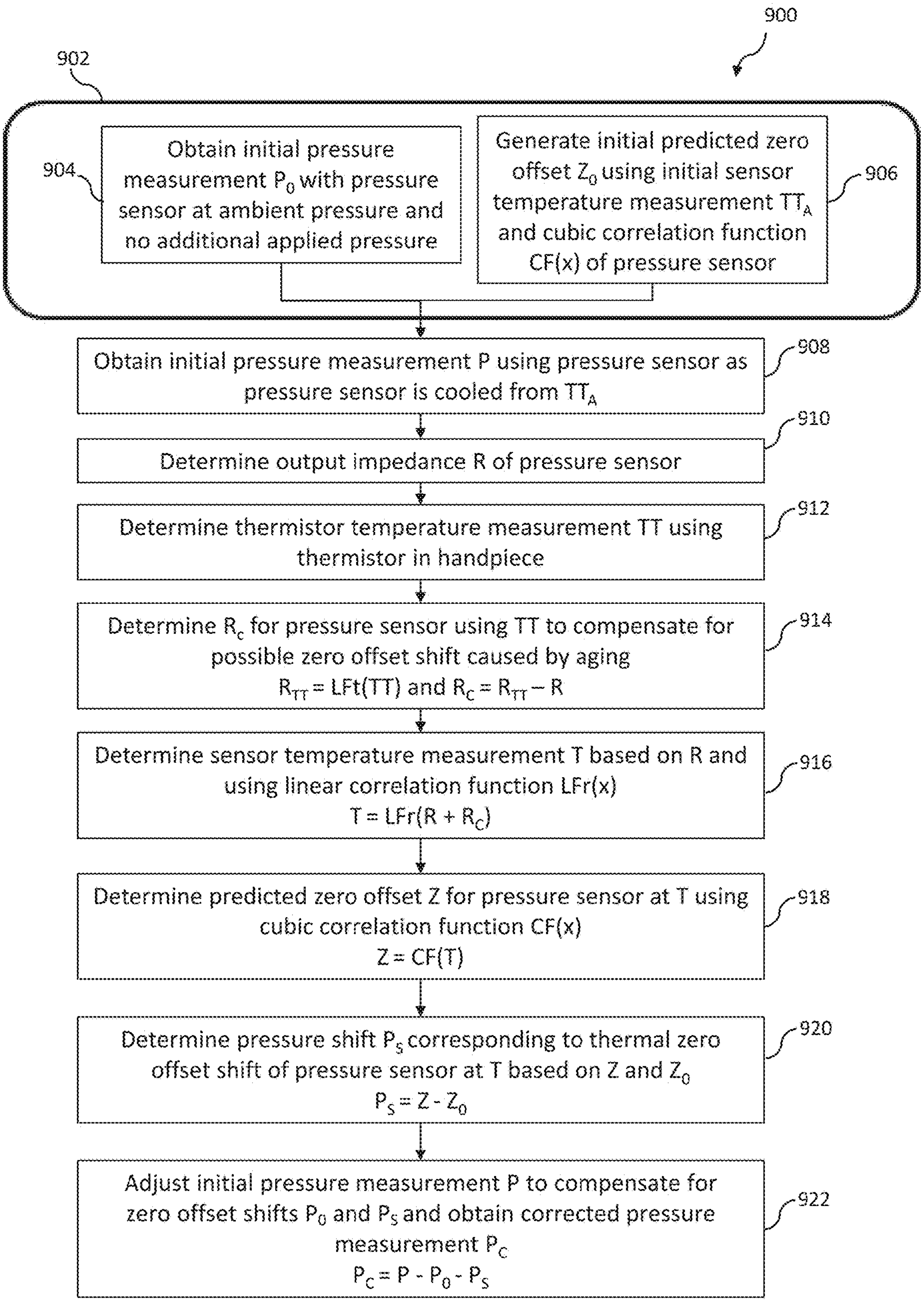
FIG. 9 is a flow diagram of an exemplary process for determining a predicted zero offset for and during use of the pressure sensor of FIG. 3 to compensate for thermal-induced zero offset shifts, according to certain embodiments of the present disclosure.

FIG. 9 is a flow diagram of an exemplary process 900 for generating a predicted zero offset shift for the pressure sensor while the pressure sensor 300 is cooling down from an elevated temperature, according to certain embodiments of the present disclosure. Process 900 may be performed by the surgical system 10 in conjunction with handpiece 118.

In some embodiments, process 900 utilizes a determined linear correlation function, LFr(x), between the output impedance of the pressure sensor 300 and the temperature of the pressure senor, and a determined cubic correlation function, CF(x), between the zero offset of the pressure sensor 300 and the temperature of the pressure senor. In certain embodiments, the determined linear correlation function, LFr(x), and the determined cubic correlation function, CF(x), may all be stored in the EEPROM 119 of the corresponding handpiece 118 and retrieved by the surgical system 10 when the handpiece 118 is connected and process 900 is performed. Additionally or alternatively, determined linear correlation function, LFr(x), and the determined cubic correlation function, CF(x), may be stored in surgical console 100, such as in memory 112 of computer system 108.

Process 900 begins at operations 904 and 906, which may be performed during an initialization phase 902 of the pressure sensor 300, after the handpiece 118 is connected to the surgical system 10 at an elevated temperature, where no strain or pressure is applied to the pressure sensor 300 therein.

At operation 904, the surgical system 10 obtains an initial pressure measurement, $P_0$, when the pressure sensor 300 in the handpiece 118 is at ambient pressure, and no additional pressure or strain is applied to the pressure sensor 300. For example, a pressure sensor (e.g., pressure sensor 300 disposed in the handpiece 118) obtains the initial pressure measurement under the conditions discussed above and, for example, communicates the measurement with computer system 108 for use in operation 922. When at ambient pressure, and with no additional pressure or strain applied to the pressure sensor 300, $P_0$ corresponds with the age induced zero offset shift of the pressure sensor 300.

At operation 906, the surgical system 10 determines an initial predicted zero offset, $Z_0$, based on the sensor temperature measurement $TT_A$ of the pressure sensor 300 inside the handpiece 118. For example, computer system 108 of surgical console 100 may determine $TT_A$ by performing operations 806, 808, and 816 of process 800 described above, retrieve the cubic correlation function, CF(x), stored in the EEPROM 119 of the handpiece 118, and apply the retrieved function to $TT_A$ to determine $Z_0$, wherein $Z_0=CF(TT_A)$.

After operations 904 and 906 are performed, the process 900 continues with operation 908 where surgical system 10 measures fluid pressure in the handpiece 118 to obtain an initial pressure measurement, P, as the handpiece 118 (and the pressure sensor 300 therein) is cooled from the initial sensor temperature $TT_A$. For example, a pressure sensor (e.g., pressure sensor 300 disposed in the handpiece 118), measures the fluid pressure in the handpiece 118 to obtain P. P may then be obtained by or communicated to computer system 108 for use in operation 922.

At operation 910, the surgical system 10 determines an output impedance, R, of the pressure sensor 300 simultaneously or sequentially after the obtaining of P at operation 908. For example, computer system 108 of surgical control 100 determines an output impedance of the pressure sensor 300 (e.g., as discussed above with reference to determining the output impedance from circuit 500 of pressure sensor 300) while pressure sensor 300 is used to measure P at operation 908.

At operation 912, the surgical system 10 obtains a thermistor temperature measurement, TT, of the pressure sensor 300 using a thermistor in the handpiece 118. For example, a thermistor (e.g., thermistor 314 coupled to the pressure sensor 300 in the handpiece 118) in the handpiece 118 is used to measure and determine TT for the pressure sensor 300. Surgical system 10 may determine TT simultaneously or sequentially with P at operation 908. Surgical system 10 may adjust TT similar to the adjustment of $TT_0$ in operation 808 of process 800.

At operation 914, the surgical system 10 determines a resistance calibration constant, $R_C$, for the pressure sensor 300 based on a difference between the output impedance R of the pressure sensor 300 obtained at operation 910 and an output impedance, $R_{TT}$, for the pressure sensor 300 determined based on the thermistor temperature measurement TT obtained in operation 912. For example, computer system 108 of surgical console 100 may determine $R_{TT}$ using TT obtained in operation 912 using operation 810 of process 800 and then perform the determination discussed above to obtain $R_C$, based on the following function: $R_C=R_{TT}-R$. In some embodiments, $R_C$ may be 0 or negligible if no age induced zero offset shift has occurred in the pressure sensor 300.

At operation 916, the surgical system 10 determines a sensor temperature measurement, T, for the pressure sensor 300 based on the output impedance R of the pressure sensor 300 determined in operation 910 and the resistance calibration constant $R_C$ determined in operation 914. For example, computer system 108 of surgical console 100 may retrieve the linear correlation function LFr(x) from the EEPROM

119 of the handpiece 118 and use it along with R and $R_C$ previously obtained to determine T, based on the following function: $T=LFr(R+R_C)$.

At operation 918, the surgical system 10 determines a predicted zero offset, Z, for the pressure sensor 300 at sensor temperature measurement T determined in operation 916 for determining a thermal induced zero offset shift of the pressure measurement P, as described below. For example, computer system 108 of surgical console 100 may retrieve the cubic correlation function CF(x) from the EEPROM 119 of the handpiece 118 and use it along with T previously obtained to determine Z, based on the following function: $Z=CF(T)$.

At operation 920, the surgical system 10 determines a pressure shift, $P_S$, based on a difference between the predicted zero offset Z determined in operation 918, and the initial predicted zero offset $Z_0$ determined at operation 906. For example, computer system 108 of surgical console 100 may perform the determination discussed above to obtain $P_S$, based on the following function: $P_S=Z-Z_0$. Pressure shift $P_S$ corresponds to the thermal induced zero offset shift of the pressure sensor 300 at T.

At operation 922, the surgical system 10 adjusts the initial pressure measurement P obtained in operation 908 with the thermal induced zero offset shift $P_S$ and age induced zero offset shift $P_0$ (if present) to obtain a corrected pressure measurement, $P_C$. For example, computer system 108 of surgical console 100 performs the adjustment (i.e., calibration) discussed above to determine $P_C$, based on the following function: $P_C=P-P_0-P_S$.

Upon determining the corrected pressure measurement $P_C$ for the measurement obtained from the pressure sensor 300 in the handpiece 118, the surgical system 10 may output $P_C$ to the user via the external display 104 connected thereto. For example, computer system 108 of surgical console 100 may cause $P_C$ to be shown on display 104 connected to surgical console 100 when the handpiece 118 and pressure sensor 300 therein is in use. In certain embodiments, the surgical system 10 may perform process 900 each time the handpiece 118 and/or the pressure sensor 300 therein is used to obtain an IOP pressure measurement.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A method for use by a surgical system, comprising:

measuring a fluid pressure in a fluid flow path of a handpiece device resulting in a fluid pressure measurement, wherein the measuring comprises using a pressure sensor disposed on the fluid flow path in the handpiece device;

determining a sensor temperature measurement of the pressure sensor, the sensor temperature measurement corresponding to a temperature of the pressure sensor when the fluid pressure was measured by the pressure sensor;

determining a predicted sensor zero offset for the pressure sensor using a zero offset correlation function and the sensor temperature measurement, wherein the zero offset correlation function comprises a mathematical polynomial function for providing the predicted sensor zero offset of the pressure sensor based on the sensor temperature measurement of the pressure sensor;

adjusting the fluid pressure measurement with the predicted sensor zero offset, resulting in an adjusted fluid pressure measurement; and outputting the adjusted fluid pressure measurement.

2. The method of claim 1, wherein obtaining the sensor temperature measurement of the pressure sensor comprises:

determining an output impedance of the pressure sensor, and determining the sensor temperature measurement of the pressure sensor based on the output impedance using a linear correlation function stored in the handpiece device, wherein the linear correlation function provides the sensor temperature measurement of the pressure sensor based on the output impedance of the pressure sensor.

3. The method of claim 1, wherein the sensor temperature measurement of the pressure sensor is between about 20° C. and about 140° C.

4. The method of claim 1, wherein the zero offset correlation for the pressure sensor is configured to provide the predicted sensor zero offset for the pressure sensor when the sensor temperature measurement of the pressure sensor is between about 20° C. and about 140° C.

5. The method of claim 1, wherein obtaining the sensor temperature measurement of the pressure sensor comprises measuring the temperature of the pressure sensor using a thermistor in the handpiece device.

6. The method of claim 2, further comprising checking the sensor temperature measurement of the pressure sensor after the sensor temperature measurement is obtained by:

obtaining a second temperature measurement of the pressure sensor using a thermistor in the handpiece device;

comparing the sensor temperature measurement to the second temperature measurement obtained by the thermistor; and confirming a difference between the sensor temperature measurement and the second temperature measurement is within a predetermined threshold.

7. The method of claim 2, wherein the pressure sensor comprises:

a sensing circuit having four semiconductor strain gages connected as a Wheatstone bridge;

a shunt resistor controlled by a shunt resistor switch and both electrically connected to the sensing circuit, the shunt resistor switch configured to operably connect and disconnect the shunt resistor from the sensing circuit; and an output shunt resistor controlled by an output shunt resistor switch and both electrically connected to the sensing circuit, the output shunt resistor switch configured to operably connect and disconnect the output shunt resistor from the sensing circuit; and wherein determining the output impedance of the pressure sensor comprises solving an equation for $R_{Sensor\ Output\ Impedance}$ and using Ohm's law as applied to the sensing circuit in the pressure sensor when the fluid pressure in the fluid flow path is measured by the pressure sensor, the equation comprising:

$$R_{Sensor\ Output\ Impedance} = \frac{(V_{Shunt} - V_{Output\ Shunt})}{V_{Output\ Shunt}} \times R_{Output};$$

wherein:

$V_{Shunt}$ is an output voltage from the pressure sensor when the shunt resistor is connected to the sensing circuit;

$V_{Output\ Shunt}$ is the output voltage from the pressure sensor when the shunt resistor and the output shunt resistor are connected in the sensing circuit; and $R_{Output}$ is about 1.5 kΩ.

8. The method of claim 6, further comprising adjusting the sensor temperature measurement using the second temperature measurement as a reference when the difference between the sensor temperature measurement and the second temperature measurement exceeds the predetermined threshold.

9. The method of claim 1, wherein determining the predicted sensor zero offset for the pressure sensor using the zero offset correlation function and the sensor temperature measurement comprises the surgical system obtaining the zero offset correlation function from the handpiece device and determining the predicted sensor zero offset based on the sensor temperature measurement, the zero offset correlation previously determined by:

heating the pressure sensor to an elevated temperature above room temperature;

collecting a plurality of sampled data corresponding to an output voltage and an output impedance of the pressure sensor at varying temperatures as the pressure sensor cools from the elevated temperature;

fitting the plurality of sampled data with a correlation curve; and deriving the zero offset correlation function from the correlation curve, wherein the zero offset correlation function is a mathematical polynomial function.

10. The method of claim 9, wherein during the collecting of the plurality of sampled data corresponding to the output impedance of the pressure sensor, determining the zero offset correlation function further comprises introducing an offset to increase a signal to noise ratio and minimize the collecting of the plurality of sampled data wherein the output voltage of the pressure sensor is 0.

11. The method of claim 9, wherein during the collecting of the plurality of sampled data, the plurality of sampled data comprises collecting alternating measurements of the output voltage and the output impedance of the pressure sensor, wherein a time between each output voltage measurement and output impedance measurement in the plurality of sampled data is less than about one second.

12. The method of claim 1, further comprising storing one or more performance parameters of the pressure sensor related to the zero offset correlation function in a memory of the handpiece device after the adjusted fluid pressure measurement is outputted.

13. A pressure sensor system for use with a handpiece device, comprising:

a pressure sensor disposed adjacent to a fluid flow path in the handpiece device, the pressure sensor comprising:

a flexible diaphragm having a pressure medium side and a circuit side;

a sensing circuit having four semiconductor strain gages connected as a Wheatstone bridge, the sensing circuit in contact with the circuit side of the flexible diaphragm;

a shunt resistor controlled by a shunt resistor switch, the shunt resistor and shunt resistor switch both electrically connected to the Wheatstone bridge; and an output shunt resistor controlled by an output shunt resistor switch, the output shunt resistor and output shunt resistor switch both electrically connected to the Wheatstone bridge;

a memory disposed in the handpiece device, the memory programmed with a predetermined zero offset correlation function, wherein the predetermined zero offset correlation function provides a predicted sensor zero offset of the pressure sensor based on a temperature measurement of the pressure sensor; and a processing unit coupled to the handpiece device, the processing unit configured to adjust a fluid pressure measurement obtained by the pressure sensor by:

receiving the fluid pressure measurement from the pressure sensor;

determining a sensor temperature measurement of the pressure sensor, the sensor temperature measurement corresponding to a temperature of the pressure sensor when the fluid pressure measurement is obtained;

determining a predicted sensor zero offset for the pressure sensor based on the sensor temperature measurement and using the predetermined zero offset correlation function stored in the memory;

adjusting the fluid pressure measurement with the predicted sensor zero offset, resulting in an adjusted fluid pressure measurement; and outputting the adjusted fluid pressure measurement.

14. The pressure sensor system of claim 13, wherein the pressure sensor is disposed with the pressure medium side of the flexible diaphragm facing the fluid flow path.

15. The pressure sensor system of claim 13, wherein the handpiece device further comprises a thermistor operable to measure a temperature of the pressure sensor, wherein the sensor temperature measurement is determined using the thermistor.

* * * * *